(12) United States Patent
Tuloup et al.

(10) Patent No.: US 6,514,486 B1
(45) Date of Patent: Feb. 4, 2003

(54) COMPOSITION FOR TOPICAL APPLICATION COMPRISING AT LEAST ONE IMINOPHENOL COMPOUND

(75) Inventors: Remy Tuloup, Paris (FR); Christian Blaise, Saint Mande (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/341,099

(22) PCT Filed: Oct. 26, 1998

(86) PCT No.: PCT/FR98/02284

§ 371 (c)(1),
(2), (4) Date: Sep. 10, 1999

(87) PCT Pub. No.: WO99/22707

PCT Pub. Date: May 14, 1999

(30) Foreign Application Priority Data

Nov. 4, 1997 (FR) ............................................. 97 13843

(51) Int. Cl.[7] .............................................. A61K 7/135
(52) U.S. Cl. ......................................... 424/62; 424/401
(58) Field of Search .................... 424/62, 43, 70.1, 424/401, DIG. 5; 514/637, 641, 844, 938, 944, 945

(56) References Cited

U.S. PATENT DOCUMENTS 2,220,065 A    11/1940    Clarkson .................... 564/276
3,182,053 A    5/1965    Steiger ........................ 534/738
4,828,568 A *  5/1989    Konrad et al. .................. 8/408
4,933,330 A *  6/1990    Jorgensen et al. .......... 514/159

FOREIGN PATENT DOCUMENTS

DE          3545245 A1 *    6/1987

OTHER PUBLICATIONS

Database HCAPLUS on STN, AN 1987:604912, DE 3545245 A1 (Konrad et al.), bibliographic data.*
Woodruff J: "Lightening Skin and Lessening Cellulite", Manufacturing Chemist, vol. 67, No. 4, Apr. 1996, p. 38, 39, 41.
Kaeding et al: "Schiff Base Phenyl N–Methylcarbamates", Journal of Agricultural and Food Chemistry, vol. 13, No. 4, p. 378–380, Jul.–Aug., 1965.

* cited by examiner

Primary Examiner—Russell Travers
Assistant Examiner—Alysia Berman

(57) ABSTRACT

The invention relates to a composition for topical application to the skin and/or its superficial growths comprising, in a cosmetically and/or dermatologically acceptable medium, at least one compound comprising an iminophenol fragment and to the use of the said compound in a composition as agent for depigmenting and/or lightening the human skin, the body hairs and/or the hair.

It also relates to a process for depigmenting and/or lightening the skin, the body hairs and/or the hair which consists in applying the abovementioned composition to the human skin, the body hairs and/or the hair.

8 Claims, No Drawings

COMPOSITION FOR TOPICAL APPLICATION COMPRISING AT LEAST ONE IMINOPHENOL COMPOUND

The present invention relates to a composition for topical application to the skin and/or its superficial growths comprising, in a cosmetically and/or dermatologically acceptable medium, at least one compound comprising an iminophenol fragment and to the use of the said compound as depigmenting or lightening agent in a cosmetic and/or dermatological composition.

The colour of the human skin depends on various factors, in particular on the seasons of the year, race and sex, and it is mainly determined by the nature and the concentration of melanin produced by the melanocytes. Melanocytes are specialized cells which synthesize melanin via specific organelles, the melanosomes. In addition, at different periods in their lives, some people witness the appearance on the skin and more especially on the hands of darker and/or more highly coloured blemishes which give the skin a heterogeneous appearance. These blemishes are also due to a high concentration of melanin in the keratinocytes situated at the surface of the skin.

In the same way, the colour of the body hairs and of the hair is due to melanin, when the body hairs or the hair are dark, some people want these to be lighter. This is particularly important for body hairs, which are less visible when they are light than when they are dark.

The mechanism of formation of the pigmentation of the skin, of the body hairs and of the hair, that is to say of the formation of melanin, is particularly complex and involves, schematically, the following main stages:

Tyrosine→Dopa→Dopaquinone→Dopachrome→Melanin

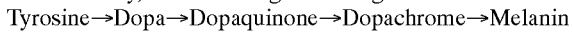

Tyrosinase (monophenol dihydroxyl phenylalanine:oxygen oxidoreductase EC 1.14.18.1) is the essential enzyme involved in this sequence of reactions. In particular, it catalyses the conversion reaction of tyrosine to Dopa (dihydroxyphenylalanine), by virtue of its hydroxylase activity, and the conversion reaction of Dopa to dopaquinone, by virtue of its oxidase activity. This tyrosinase only acts when it is in the maturation state under the effect of certain biological factors.

A substance is recognized as depigmenting if it acts directly on the vitality of the epidermal melanocytes where melanogenesis takes place and/or if it interferes with one of the stages in the biosynthesis of melanin, either by inhibiting one of the enzymes involved in melanogenesis or by being inserted as structural analogue of one of the chemical compounds in the sequence for the synthesis of melanin, which sequence can then be blocked and thus ensure depigmentation.

The substances most commonly used as depigmenting agents are more particularly hydroquinone and its derivatives, in particular its ethers, such as hydroquinone monomethyl ether and monoethyl ether. These compounds, although they are certain to be effective, are unfortunately not free of side effects due to their toxicity, which can make their use problematic or indeed dangerous. This toxicity arises from their intervention in fundamental mechanisms of melanogenesis, killing cells which then risk disturbing their biological environment and which consequently oblige the skin to discharge them, producing toxins.

Thus, hydroquinone is a compound which is particularly irritating and cytotoxic for melanocytes, the complete or partial replacement of which has been envisaged by many writers.

A search has thus been carried out for substances which do not interfere in the mechanism of melanogenesis but which act upstream on tyrosinase, preventing its activation, and which are, for this reason, much less toxic. Use is commonly made, as inhibitor of the activation of tyrosinase, of kojic acid, which complexes the copper present in the active site of this enzyme. Unfortunately, this compound can cause allergic reactions ("Contact allergy to kojic acid in skin care products", Nakagawa M. et al., in Contact Dermatitis, Jan. 95, Vol. 42 (1), pp. 9–13). This compound is also unstable in solution, which somewhat complicates the manufacture of the composition.

The use of inoffensive topical depigmenting substances which are highly effective is very particularly sought after with a view to treating regional hyperpigmentations by melanocytic hyperactivity, such as idiopathic melasmas, arising during pregnancy ("mask of pregnancy" or chloasma) or oestrone/progestogen contraception, localized hyperpigmentation by benign melanocytic hyperactivity and proliferation, such as senile pigmental blemishes known as actinic lentigines, accidental hyperpigmentations or depigmentations, possibly due to photo-sensitization or to post-lesional healing, as well as certain leucodermas, such as vitiligo. For the latter conditions (healing which can result in a scar giving the skin a whiter appearance and leucodermas), for want of being able to repigment the damaged skin, the end result is to depigment the remaining normal skin regions to give the whole skin a homogeneous white colouring.

The need consequently remains for a novel lightening agent for the human skin, body hairs and/or hair with an action as effective as those known but which does not have their disadvantages, that is to say which is non-irritating, non-toxic and/or non-allergizing for the skin and which is stable in a composition.

The Applicant Company has unexpectedly found that compounds comprising an iminophenol fragment exhibit a depigmenting activity, even at low concentrations, without showing cytotoxicity.

Compounds with an iminophenol fragment which can be used as antipathogens, antivirals or antibacterials and which are intended to be administered orally or parenterally are known from U.S. Pat. No. 3,182,053. In addition, certain compounds with an iminophenol fragment which can be used as antioxidants for fuel, rubber and other auto-oxidizable materials are known from U.S. Pat. No. 2,220,065.

However, to the knowledge of the Applicant Company, provision has never yet been made to administer compounds with an iminophenol fragment by the topical route, in particular for the purpose of lightening or depigmenting the skin or its superficial growths. The subject-matter of the present invention is therefore a composition for topical application to the skin and/or its superficial growths comprising, in a cosmetically and/or dermatologically acceptable medium, at least one compound of following formula (I):

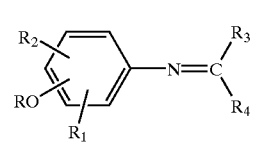

(I)

in which:
R represents a group chosen from:
the hydrogen atom;
a saturated or unsaturated, linear, branched or cyclic $C_1$–$C_{24}$ alkyl group which is optionally hydroxylated by one or more hydroxyl functional groups;

an aryl group which is unsubstituted or substituted by one or more functional groups chosen from: —OH, —NH$_2$, —COOH, —NO$_2$, —OR$_5$ with R$_5$=C$_1$–C$_{24}$ alkyl, —COOR$_6$ with R$_6$=C$_1$–C$_{24}$ alkyl, or —NR$_7$R$_8$ with R$_7$=H or C$_1$–C$_{24}$ alkyl and R$_8$=H or C$_1$–C$_{24}$ alkyl;

a —COR$_9$ group, R$_9$ representing a saturated or unsaturated, linear, branched or cyclic C$_1$–C$_{24}$ alkyl group which is optionally hydroxylated by one or more hydroxyl functional groups or an aryl group which is unsubstituted or substituted by one or more functional groups chosen from —OH, —NH$_2$, —COOH, —NO$_2$, —OR$_5$, —COOR$_6$ or —NR$_7$R$_8$ in which R$_5$, R$_6$, R$_7$ and R$_8$ have the same definition as above;

R$_1$, R$_2$, R$_3$ and R$_4$, which are identical or different, represent a group chosen from:

the hydrogen atom;

a saturated or unsaturated, linear, branched or cyclic C$_1$–C$_{24}$ alkyl group which is optionally hydroxylated by one or more hydroxyl functional groups;

an aryl group which is unsubstituted or substituted by one or more functional groups chosen from —OH, —NH$_2$, —COOH, —NO$_2$, —OR$_5$, —COOR$_6$ or —NR$_7$R$_8$ in which R$_5$, R$_6$, R$_7$ and R$_8$ have the same definition as above;

a group chosen from: —OH, —OQ$_1$, —COQ$_2$, —COOQ$_3$, —NQ$_4$Q$_5$, —CONQ$_6$Q$_7$, —SQ$_8$ or —CH$_2$OQ$_9$, Q$_1$, Q$_2$, Q$_3$, Q$_4$Q$_5$, Q$_6$, Q$_7$, Q$_8$ and Q$_9$ being chosen from the hydrogen atom, saturated or unsaturated, linear, branched or cyclic C$_1$–C$_{24}$ alkyl groups which are optionally substituted by one or more hydroxyl groups or aryls which are unsubstituted or substituted by one or more functional groups chosen from: —OH, —NH$_2$, —COOH, —NO$_2$, —OR$_5$, —COOR$_6$ or —NR$_7$R$_8$ in which R$_5$, R$_6$, R$_7$ and R$_8$ have the same definition as above;

residues of amino acids and of carbohydrates which are cyclic or non-cyclic.

These compounds exhibit the advantage of being easy to obtain. They can be obtained in particular by reacting an aminophenol with a carbonyl compound: ketone or aldehyde. The carbonyl reactant can optionally be used in acetal form.

According to the present invention, mention may advantageously be made, among linear or branched alkyl radicals having from 1 to 24 carbon atoms, of the methyl, ethyl, propyl, isopropyl, butyl, tert-butyl, hexyl, octyl, nonyl, 2-ethylhexyl and dodecyl radicals.

Mention may in particular be made, among linear alkyl radicals having from 1 to 24 carbon atoms, of the methyl, ethyl, propyl, octyl, dodecyl, hexadecyl, behenyl and octadecyl radicals.

Mention may in particular be made, among branched alkyl radicals having from 1 to 24 carbon atoms, of the 2-ethylhexyl, 2-butyloctyl and 2-hexyldecyl radicals.

Mention may more particularly be made, among unsaturated alkyl radicals, of the allyl radical.

When the alkyl radical is cyclic, mention may in particular be made of the cyclohexyl, cholesteryl or tert-butylcyclohexyl radical.

The compounds of formula (I) of the present invention are preferably those for which at least one and preferably all of the conditions below are observed:

R represents a hydrogen atom,

OR is in the ortho or para position with respect to the imine functional group,

R$_3$=H,

R$_4$ represents an —NQ$_4$Q$_5$ group as defined above.

The preferred compound of formula (I) is N'-(4-hydroxyphenyl)-N,N-dimethylformamidine.

In comparison with the compounds of the prior art known as depigmenting agents, the compounds of formula (I) exhibit the advantage of being more stable and more efficient, as will be shown in the tests below.

The cosmetic or dermatological composition according to the invention is advantageously intended to depigment and/or lighten the human skin and/or to remove pigmental blemishes from the skin and/or to depigment the body hairs and/or the hair.

Another subject-matter of the present invention is the use of the abovementioned compounds of formula (I) in a cosmetic composition as inhibitor of tyrosinase and/or of the synthesis of melanin.

Another subject-matter of the invention is the use of these compounds of formula (I) in the manufacture of a dermatological composition intended to depigment and/or lighten the human skin and/or to remove pigmental blemishes from the skin and/or to depigment the body hairs and/or the hair.

Another subject-matter of the present invention is the use of these compounds of formula (I) in a cosmetic composition which depigments and/or lightens the human skin, the body hairs or the hair.

The present invention also relates to a cosmetic process for depigmenting and/or lightening the human skin, the body hairs or the hair which consists in applying a cosmetic composition according to the invention to the skin, the body hairs or the hair.

The composition according to the invention is appropriate for a topical use and therefore comprises a cosmetically or dermatologically acceptable medium, that is to say a medium compatible with the skin, the body hairs or the hair.

The derivatives of formula (I) can in particular be present in the composition in an amount ranging from 0.001 to 10% and preferably from 0.005 to 5% of the total weight of the composition.

The composition of the invention can be provided in all the pharmaceutical dosage forms normally used for a topical application, in particular in the form of an aqueous, aqueous/alcoholic or oily solution, of an oil-in-water or water-in-oil or multiple emulsion, of an aqueous or oily gel, of a liquid, pasty or solid anhydrous product, or of a dispersion of oil in an aqueous phase with the help of spherules, it being possible for these spherules to be polymeric nanoparticles, such as nanospheres and nanocapsules, or better still lipid vesicles of ionic and/or non-ionic type.

This composition can be more or less fluid and have the appearance of a white or coloured cream, of an ointment, of a milk, of a lotion, of a serum, of a paste or of a foam. It can optionally be applied to the skin or to the hair in aerosol form. It can also be provided in solid form, for example in stick form. It can be used as care product and/or as make-up product. It can also be in a shampoo or conditioner form.

In a known way, the composition of the invention can also comprise adjuvants usual in the cosmetic and dermatological fields, such as hydrophilic or lipophilic gelling agents, hydrophilic or lipophilic active principles, preservatives, antioxidants, solvents, fragrances, fillers, screening agents, pigments, odour absorbers and colouring materials. The amounts of these various adjuvants are those conventionally used in the fields under consideration, for example from 0.01 to 20% of the total weight of the composition. These adjuvants, depending on their nature, can be introduced into the fatty phase, into the aqueous phase, into the lipid vesicles and/or into the nanoparticles.

When the composition of the invention is an emulsion, the proportion of the fatty phase can range from 5 to 80% by weight and preferably from 5 to 50% by weight with respect to the total weight of the composition. The oils, the emulsifiers and the coemulsifiers used in the composition in emulsion form are chosen from those conventionally used in the field under consideration. The emulsifier and the coemulsifier are present in the composition in a proportion ranging from 0.3 and 30% by weight and preferably from 0.5 to 20% by weight with respect to the total weight of the composition. Mention may be made, as oils which can be used in the invention, of mineral oils (liquid petrolatum), oils of vegetable origin (avocado oil, soybean oil), oils of animal origin (lanolin), synthetic oils (perhydro-squalene), silicone oils (cyclomethicone) and fluorinated oils (perfluoropolyethers). Use may also be made, as fatty substances, of fatty alcohols (cetyl alcohol), fatty acids or waxes (carnauba wax, ozokerite).

Mention may be made, as emulsifiers and coemulsifiers which can be used in the invention, for example, of esters of fatty acid and of polyethylene glycol, such as PEG-20 stearate, and esters of fatty acid and of glycerol, such as glyceryl stearate.

Mention may in particular be made, as hydrophilic gelling agents, of carboxyvinyl polymers (carbomer), acrylic copolymers, such as acrylate/alkyl acrylate copolymers, polyacrylamides, polysaccharides, natural gums, and clays and mention may be made, as lipophilic gelling agents, of modified clays, such as bentones, metal salts of fatty acids, hydrophobic silica and polyethylenes.

Use may in particular be made, as active principles, of polyols (glycerol, propylene glycol), vitamins, keratolytic and/or desquamative agents (salicylic acid and its derivatives, alpha-hydroxy acids, ascorbic acid and its derivatives), anti-inflammatory agents, soothing agents and their mixtures. The compounds of formula (I) can also be used in combination with other depigmenting agents, such as kojic acid or hydroquinone and its derivatives, which makes it possible to use the latter at doses which are less toxic for the skin. In the event of incompatibility, these active principles and/or the compounds of formula (I) can be incorporated in spherules, in particular vesicles, which vesicles may be ionic or non-ionic, and/or nanoparticles (nanocapsules and/or nanospheres), so as to isolate them from one another in the composition.

The invention will now be illustrated using the examples which follow. The concentrations are given as percentage by weight.

Compound Example

Preparation of N'-(4-hydroxyphenyl)-N,N-dimethylformamide

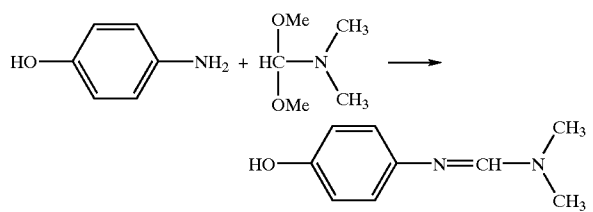

10 g of para-aminophenol and 13.4 ml of N,N-dimethylformamide dimethyl acetal are introduced into 100 ml of methanol and the mixture is brought to reflux for 30 minutes. After cooling, N'-(4-hydroxyphenyl)-N,N-dimethylformamidine precipitates. It is recrystallized from ethanol. The melting temperature of the product obtained is 218° C. The elemental analysis is in accordance with the expected structure.

Tests

A biological test demonstrated the depigmenting activity of the compounds of formula (I).

This test corresponds to that described in Patent FR 2,734,825, filed by the Applicant Company, and in the article by R. Schmidt, P. Krien and M. Régnier, Anal. Biochem., 235(2), 113–18 (1996). This test is thus carried out on a coculture of keratinocytes and of melanocytes.

The IC50 value, which corresponds to the micromolar concentration ($\mu$M) at which 50% inhibition of melanogenesis is observed, is determined for each compound tested.

Furthermore, a category is given to each of these compounds for their maximum depigmenting activity:

category 1: 10 to 30% inhibition of melanogenesis with respect to the control (same experiment without compound to be tested);

category 2: 30 to 60% inhibition of melanogenesis with respect to the control (same experiment without compound to be tested);

category 3: 60 to 100% inhibition of melanogenesis with respect to the control (same experiment without compound to be tested).

The results are collated in the table below:

|  | IC50 ($\mu$M) | Category |
| --- | --- | --- |
| Kojic acid | 500 $\mu$M | 2 at 500 $\mu$M |
| N'-(4-Hydroxyphenyl)-N,N-dimethylformamidine | 200 $\mu$M | 2 at 50 $\mu$M |

These compounds of formula (I) therefore exhibit a greater depigmenting efficiency than kojic acid. In addition, they have the advantage of not exhibiting cytotoxicity with regard to keratinocytes and melanocytes, a major failing of the depigmenting agents known before.

EXAMPLES OF COMPOSITIONS

Example 1

Treating Cream

| Cetyl alcohol | 1.05% |
| --- | --- |
| PEG-20 stearate (Myrj 49, sold by the company ICI) | 2% |
| Cyclomethicone | 6% |
| N'-(4-Hydroxyphenyl)-N,N-dimethyl-formamidine | 0.5% |
| Carbomer | 0.6% |
| Glycerol | 3% |
| Triethanolamine | 1% |
| Preservatives | 0.5% |
| Demineralized water | q.s. for 100% |

The cream obtained, applied daily, makes it possible to obtain a lightening of the skin.

Example 2

Treating Gel

| | |
|---|---|
| Propylene glycol | 10% |
| Ethyl alcohol | 40% |
| Glycerol | 3% |
| N'-(4-Hydroxyphenyl)-N,N-dimethyl-formamidine | 0.5% |
| Preservatives | 0.15% |
| Fragrance | 0.15% |
| Demineralized water | q.s. for 100% |

The gel obtained can be used daily and is capable of depigmenting the skin.

Example 3

Treating Stick

| | |
|---|---|
| Carnauba wax | 5% |
| Ozokerite | 7% |
| Lanolin | 6% |
| Titanium dioxide (pigments) | 20% |
| Rice starch (filler) | 7% |
| EDTA | 0.1% |
| N'-(4-Hydroxyphenyl)-N,N-dimethyl-formamidine | 2% |
| Perhydrosqualene | q.s. for 100% |

The stick obtained, used on pigmental blemishes, makes it possible to tone them down, indeed even to make them disappear.

What is claimed is:

1. A composition comprising at least one of a cosmetically acceptable medium and a dermatological acceptable medium, and at least one compound of the following formula (I):

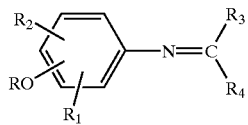

(I)

in which:

R is a hydrogen atom;

—OR is in the ortho or para position with respect to the imine functional group;

$R_1$, and $R_2$, which are identical or different, are selected from the group consisting of:

a hydrogen atom;

a saturated or unsaturated, linear, branched or cyclic $C_1$–$C_{24}$ alkyl group which is optionally hydroxylated by one or more hydroxyl functional groups;

an aryl group which is unsubstituted or substituted by one of or more functional groups which are —OH, —NH$_2$, —COOH, —NO$_2$, —OR$_5$, —COOR$_6$ or —NR$_7$R$_8$ in which $R_5$=$C_1$–$C_{24}$ alkyl, $R_6$=$C_1$–$C_{24}$ alkyl, $R_7$=H or $C_1$–$C_{24}$ alkyl and $R_8$=H or $C_1$–$C_{24}$ alkyl;

a group which is: —OH, OQ$_1$, —COQ$_2$, —COOQ$_3$, —NQ$_4$Q$_5$, —CONQ$_6$Q$_7$, —SQ$_8$ or —CH$_2$OQ$_9$, $Q_1$, $Q_2$, $Q_3$, $Q_4$, $Q_5$, $Q_6$, $Q_7$, $Q_8$ and $Q_9$ which are a hydrogen atom, saturated or unsaturated, linear, branched or cyclic $C_1$–$C_{24}$ alkyl groups which are optionally substituted by one or more hydroxyl groups or aryl groups which are unsubstituted or substituted by one or more functional groups which are: —OH, —NH$_2$, —COOH, —NO$_2$, —OR$_5$, —COOR$_6$ or —NR$_7$R$_8$ in which $R_5$, $R_6$, $R_7$ and $R_8$ have the same definition as above;

and functional groups of amino acids and of carbohydrates which are cyclic or non-cyclic;

$R_3$ is a hydrogen atom; and $R_4$ represents —NQ$_4$Q$_5$ in which $Q_4$ and $Q_5$ have the same definition as above.

2. A composition according to claim 1, wherein the compound is N'-(4-hydroxyphenyl)-N,N-dimethylformamidine.

3. A composition according to claim 1, wherein said compound of formula (I) is present in an amount ranging from 0.001 to 10% of the total weight of the composition.

4. The composition according to claim 3, wherein the composition additionally comprises at least one active principle chosen from keratolytic, desquamative agents, anti-inflammatory agents, soothing agents, other depigmenting agents and their mixtures.

5. A process for depigmenting or lightening, or combinations thereof, human skin, body hairs or hair, which comprises applying a composition according to one of the preceding claims 1, 2, 3, or 4 to human skin, body hairs or hair, or combinations thereof.

6. A process for depigmenting or lightening, or combinations thereof, human skin, body hairs or hair, or combinations thereof, which comprises applying a composition as defined in claim 1, which inhibits tyrosinase or the synthesis of melanin, or combinations thereof, to human skin, body hairs or hair, or combinations thereof.

7. A process for depigmenting or lightening, or combinations thereof, human skin, body hairs or hair, or combinations thereof, which comprises applying a composition as defined in claim 2, which inhibits tyrosinase or the synthesis of melanin, or combinations thereof, to human skin, body hairs or hair, or combinations thereof.

8. A composition according to claim 1, wherein said compound of formula (I) is present in an amount ranging from 0.005 to 5% of the total weight of the composition.

* * * * *